United States Patent
Nichols et al.

(10) Patent No.: US 9,739,383 B2
(45) Date of Patent: Aug. 22, 2017

(54) MULTI-PATH SELECTOR VALVE

(71) Applicant: IDEX Health & Science LLC, Northbrook, IL (US)

(72) Inventors: Jon A. Nichols, Forestville, CA (US); James Smyth, Rohnert Park, CA (US)

(73) Assignee: IDEX Health & Science LLC, Northbrook, IL (US)

( * ) Notice: Subject to any disclaimer, the term of this patent is extended or adjusted under 35 U.S.C. 154(b) by 0 days.

(21) Appl. No.: 14/811,637

(22) Filed: Jul. 28, 2015

(65) Prior Publication Data

US 2016/0033049 A1 Feb. 4, 2016

Related U.S. Application Data

(60) Provisional application No. 62/030,454, filed on Jul. 29, 2014, provisional application No. 62/090,250, filed on Dec. 10, 2014.

(51) Int. Cl.
*F16K 11/074* (2006.01)
*G01N 30/38* (2006.01)
(Continued)

(52) U.S. Cl.
CPC ........ *F16K 11/074* (2013.01); *F16K 11/0743* (2013.01); *G01N 30/20* (2013.01);
(Continued)

(58) Field of Classification Search
CPC ... F16K 11/074; F16K 11/0743; G01N 30/20; G01N 30/38
See application file for complete search history.

(56) References Cited

U.S. PATENT DOCUMENTS 3,747,630 A * 7/1973 Hurrell ................. F16K 11/074
137/312
4,068,528 A * 1/1978 Gundelfinger ......... G01N 30/20
73/864.84
(Continued)

FOREIGN PATENT DOCUMENTS

WO WO2008/140377 11/2008

OTHER PUBLICATIONS

GB Search Report dated Dec. 10, 2015 from International Application No. GB1513332.5.

*Primary Examiner* — Craig Schneider
*Assistant Examiner* — Kevin Barss
(74) *Attorney, Agent, or Firm* — Beyer law Group LLP

(57) ABSTRACT

A multi-path selector valve used in liquid chromatography and other analytical methods for directing fluid along alternate paths of a flowstream. The selector valve has a stator and a rotor. The dynamic face of the stator has a plurality of openings arranged along an inner ring, a plurality of openings arranged along an outer ring, and an annular collection groove formed in the dynamic face. The inner ring, outer ring, and annular collection groove are concentric circles. The rotor's dynamic face is configured to mate with the rear face of the stator, and has two fluid flow paths. One fluid flow path has one end at a rotational center of the rotor and another end of the fluid flow path is configured to be aligned with a stator opening along the inner ring. The second fluid flow path has one end that is configured to be aligned with the annular collection groove and another end that is configured to be aligned with a stator opening along the outer ring.

20 Claims, 13 Drawing Sheets

(51) Int. Cl.
*G01N 30/20* (2006.01)
*G01N 30/46* (2006.01)

(52) U.S. Cl.
CPC .......... *G01N 30/38* (2013.01); *G01N 30/468* (2013.01); *G01N 2030/201* (2013.01); *G01N 2030/202* (2013.01)

(56) References Cited

U.S. PATENT DOCUMENTS

| | | | |
|---|---|---|---|
| 5,207,109 A * | 5/1993 | Olsen | G01N 30/20 73/863.73 |
| 5,803,117 A | 9/1998 | Olsen et al. | |
| 6,012,487 A * | 1/2000 | Hauck | F16K 11/0743 137/625.11 |
| 6,012,488 A * | 1/2000 | Nichols | F16K 11/0743 137/625.11 |
| 6,453,946 B2 * | 9/2002 | Nichols | F16K 11/074 137/625.15 |
| 6,672,336 B2 * | 1/2004 | Nichols | F16K 11/074 137/625.11 |
| 6,889,710 B2 * | 5/2005 | Wagner | B01D 53/0462 137/625.46 |
| 7,213,615 B2 * | 5/2007 | Cueni | F16K 11/0743 137/625.46 |
| 8,186,382 B2 * | 5/2012 | Wilen | F16K 11/074 137/625.46 |
| 8,236,175 B2 * | 8/2012 | Maeda | F16K 11/0743 210/198.2 |
| 2007/0053798 A1 * | 3/2007 | Johnson | B01J 19/0046 422/400 |

* cited by examiner

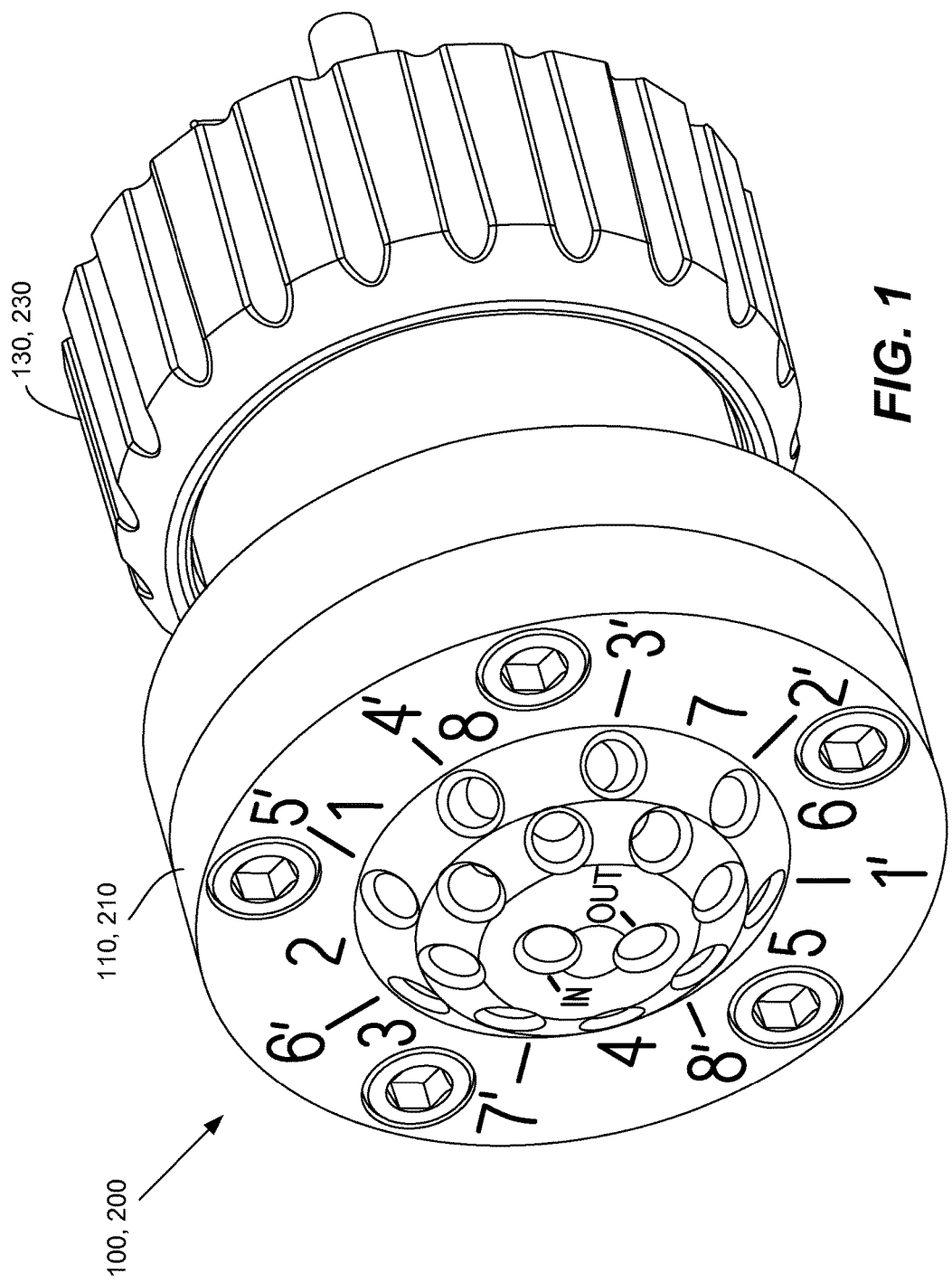

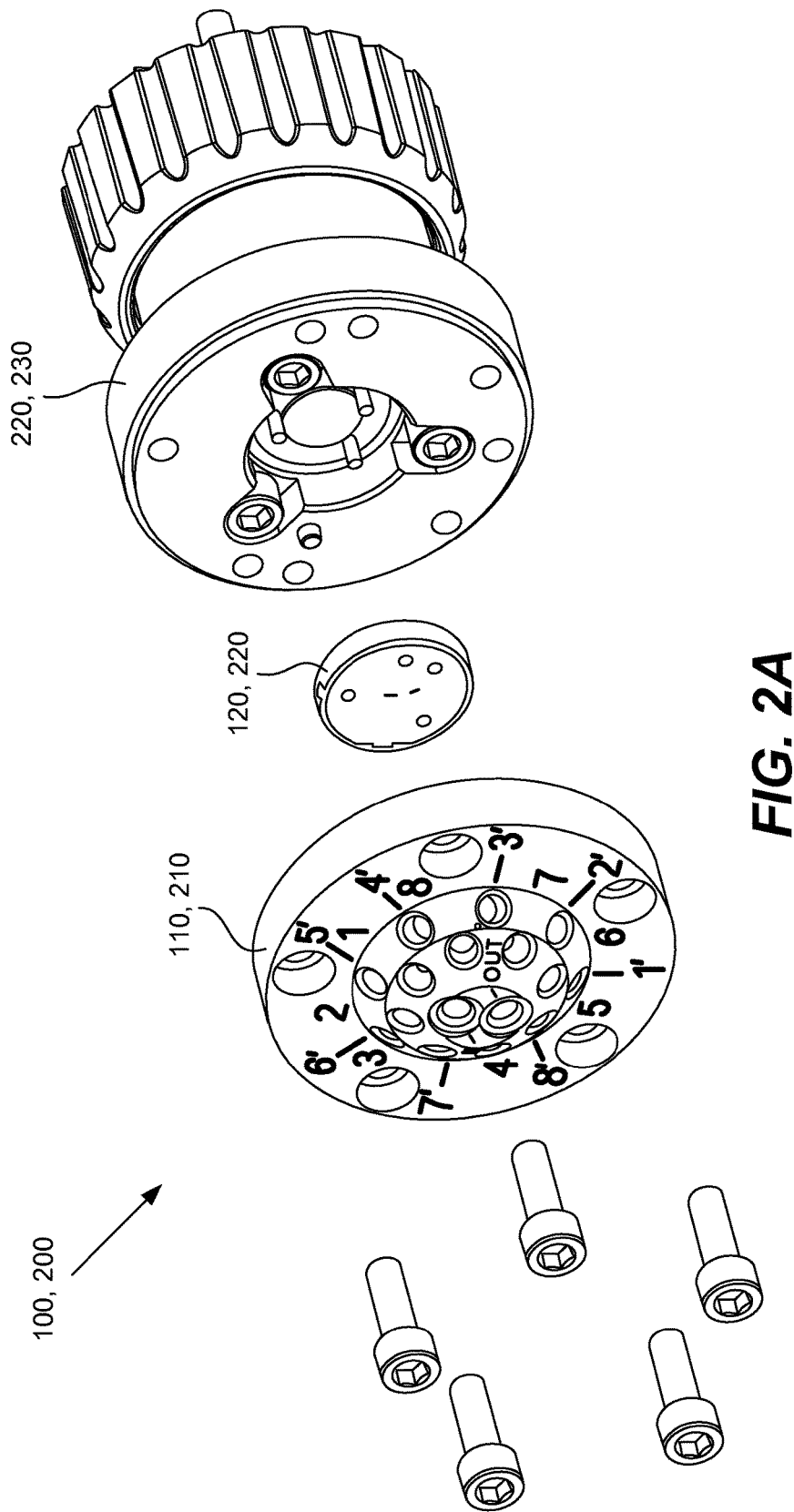

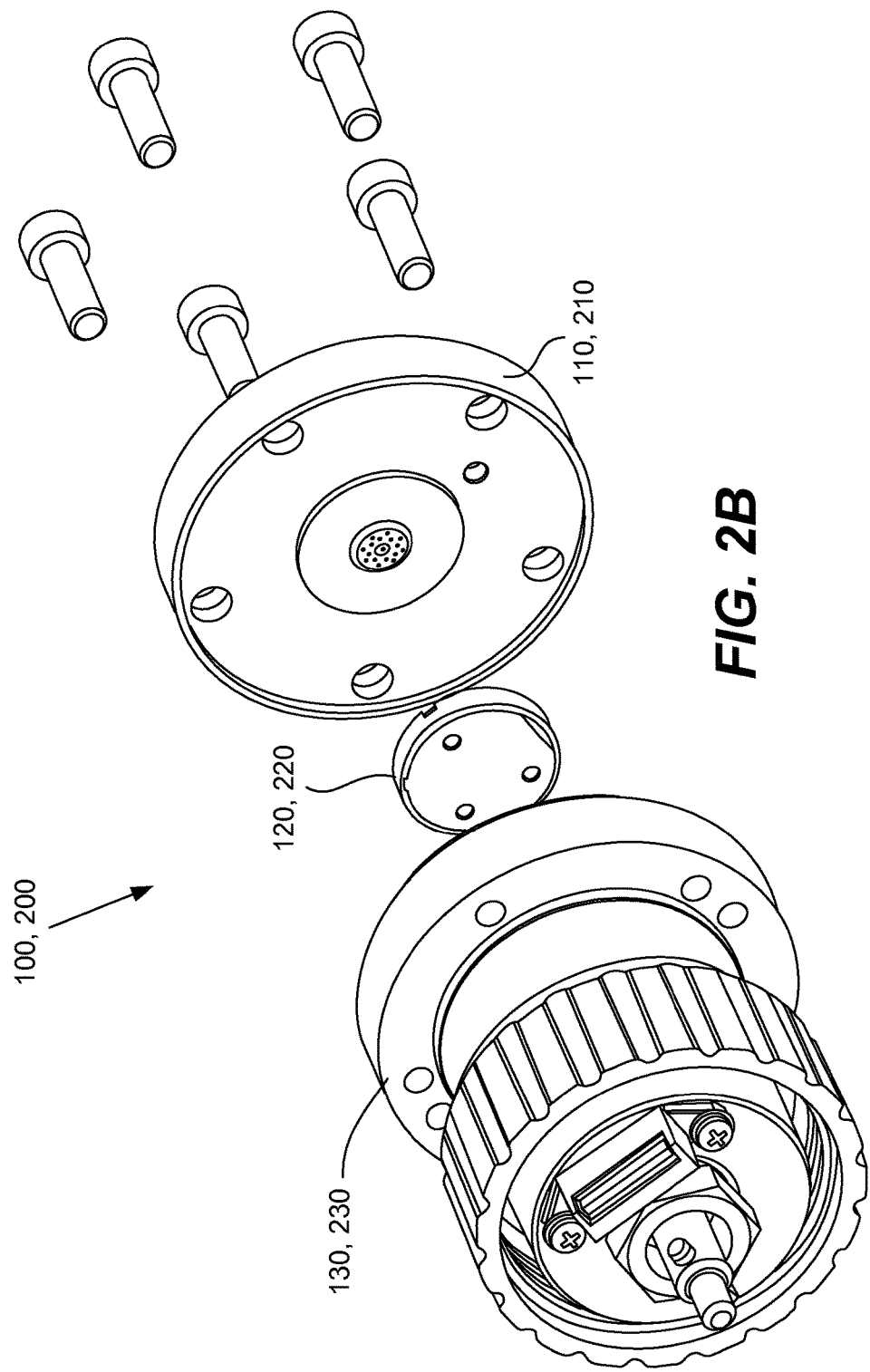

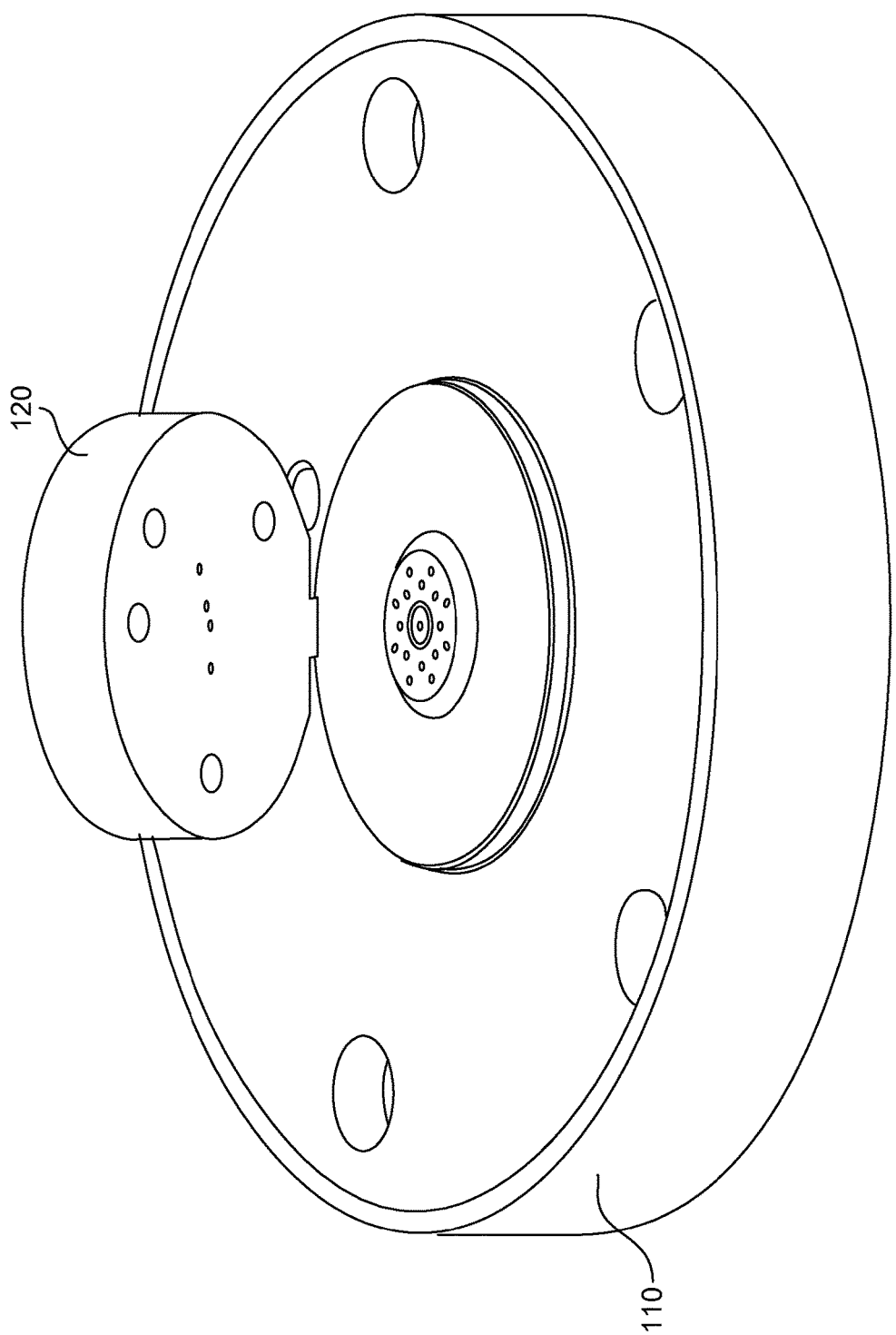

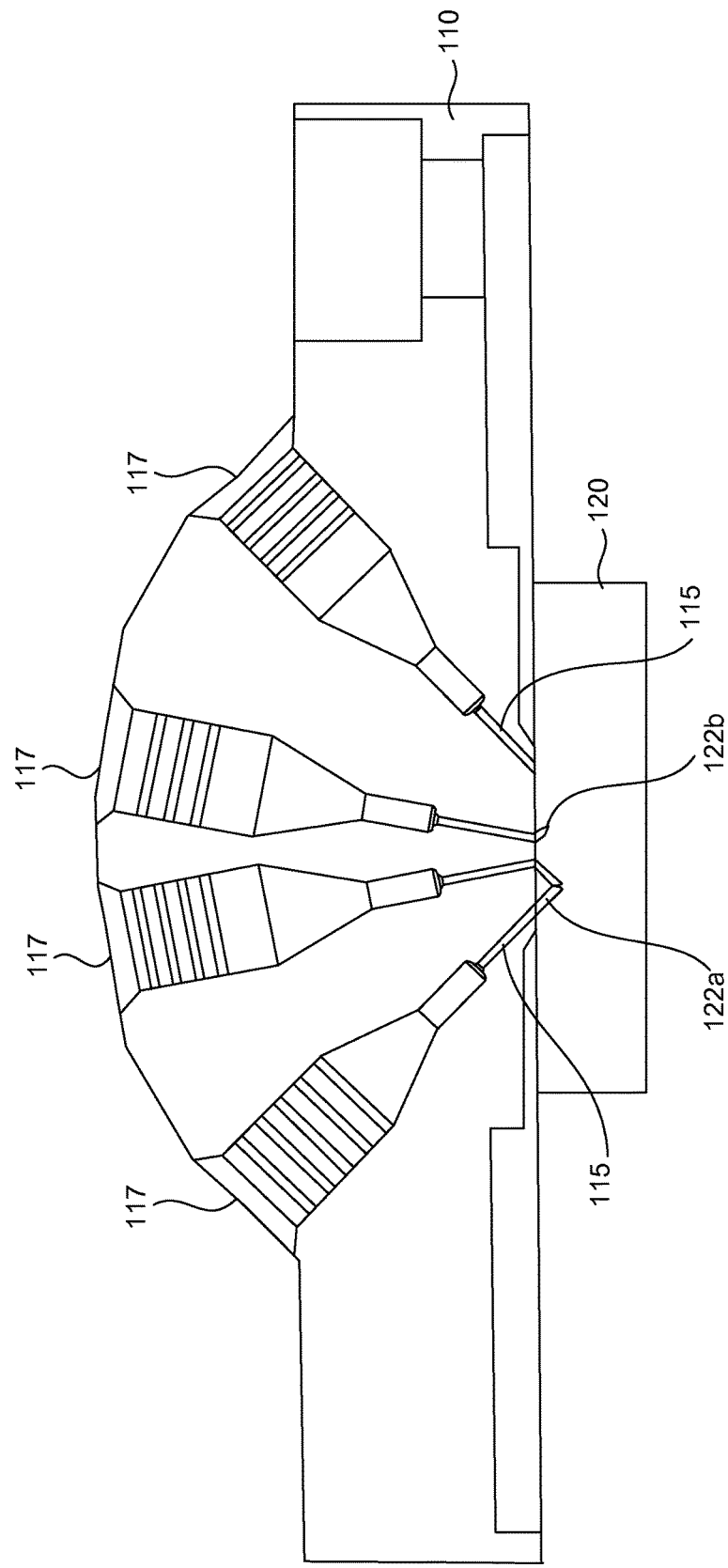

MULTI-PATH SELECTOR VALVE

RELATED APPLICATIONS

This application claims the benefit of U.S. Provisional Patent Application No. 62/030,454, filed Jul. 29, 2014, entitled "MULTI-PATH SELECTOR VALVE" and of U.S. Provisional Patent Application No. 62/090,250, filed Dec. 10, 2014, entitled "MULTI-PATH SELECTOR VALVE." The foregoing provisional applications are hereby incorporated herein by reference in their entireties.

FIELD OF THE INVENTION

The present invention relates generally to selector valves used in liquid chromatography and other analytical methods that direct fluid along alternate paths of a flowstream. More particularly, the invention relates to selector valves that allow for selection among alternate flow paths.

BACKGROUND OF THE INVENTION

High pressure liquid chromatography selector valves typically employ a stator element and a rotor device with a fluid-tight seal at the rotor/stator interface therebetween. Selector valves are typically used to direct fluid along alternate flow paths. For example, alternate columns along a flow path can be selected using a selector valve.

One type of selector includes a disk shaped rotor with channels on its front face that face holes or ports in the rear face of the stator. Rotation of the rotor, which is rotated by a motor-driven shaft, allows channels to connect to different columns depending on the position of the valve. In a typical valve, selection may be limited to only two alternate paths. Another type of selector valve has a radial groove in the rotor and an additional center port in the stator. By rotating the rotor, connection of any number of radial ports can be alternately made to the common center port. However, for such a selector valve assembly, a second selector valve is needed to redirect the flow to the alternate path. Yet another type of selector valve, described in U.S. Pat. No. 5,803,117 (which is hereby incorporated herein for all purposes), provides a single selector valve that allows selection from among three alternate routes, using channels formed in the rotor face. The selector valve described in U.S. Pat. No. 5,803,117 is a dual selector valve that uses one half of the stator face for input ports and the other side of the stator face for output ports. This arrangement of ports results in fairly good dispersion, but poor port-packing density.

While these valves are reliable, efficient, and highly successful, they often have limited switching options due to the relatively small surface area of the rotor face and the path of the fluid channel, or two selector valves may be necessary for selecting among additional alternate paths. Typically, there is relatively little surface area on the rotor face to provided additional switching options. Accordingly, there is a need to provide a single selector valve that has additional functionality while minimizing the surface area of the rotor face.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawings, in which:

FIG. 1 is a front perspective view of a dual selector valve in accordance with embodiments described herein;

FIG. 2A is an exploded front perspective view of a dual selector valve in accordance with embodiments described herein;

FIG. 2B is an exploded rear perspective view of a dual selector valve in accordance with embodiments described herein;

FIG. 3C is a perspective view of the interfacing dynamic surfaces of the stator and rotor shown in FIGS. 3A and 3B;

FIG. 3D is a side cross-sectional view of the dynamic surfaces of the stator and rotor of FIGS. 3A-3C, with the stator and rotor in fluid communication with one another.

DETAILED DESCRIPTION OF THE INVENTION

Figure 3A:
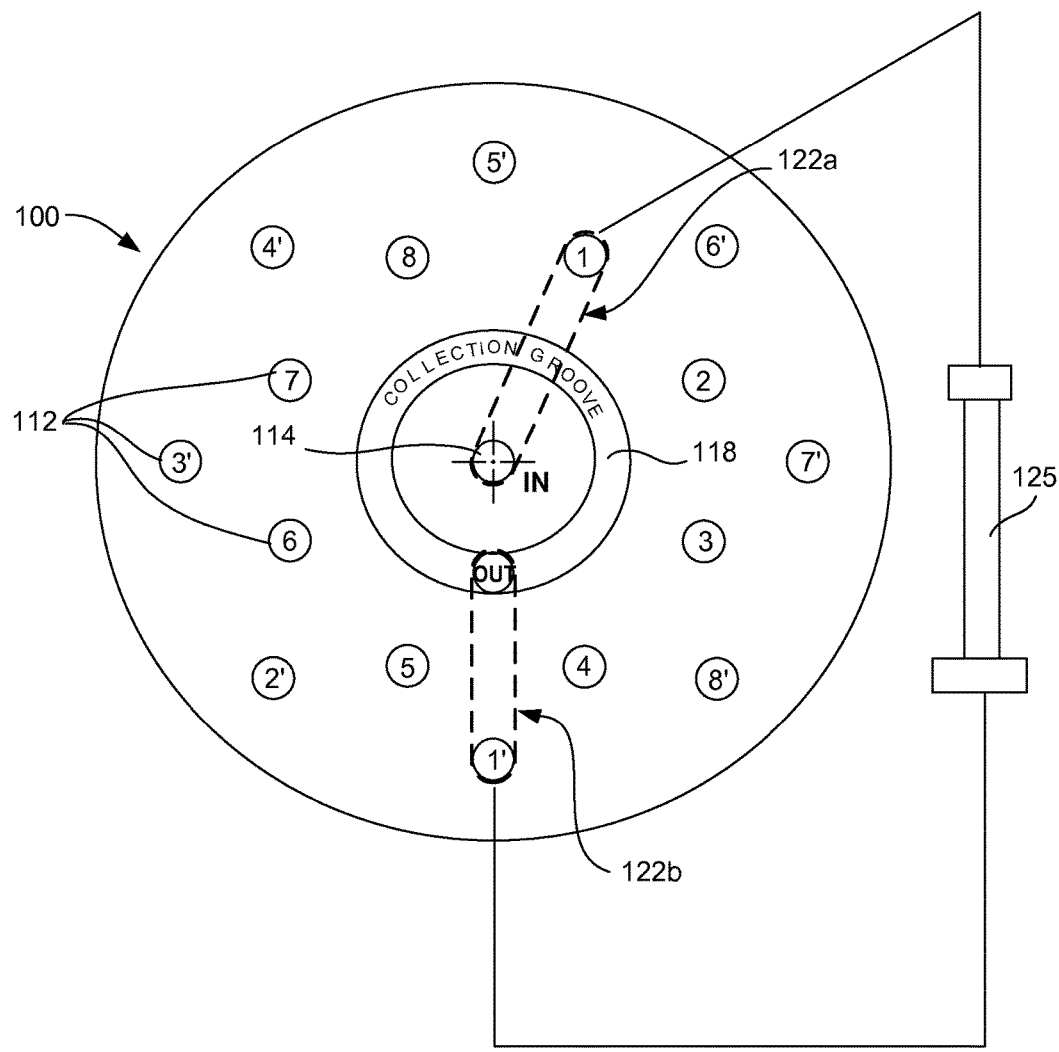
FIG. 3A is a simplified plan view of an embodiment of the stator face at the stator-rotor interface of an embodiment of a dual selector valve.

While the present invention will be described with reference to a few specific embodiments, the description is illustrative of the invention and is not to be construed as limiting the invention. Various modifications to the present invention can be made to the embodiments described herein by those skilled in the art without departing from the true spirit and scope of the invention as defined by the appended claims.

FIGS. 1-2B are perspective views of a dual selector valve assembly 100, 200 in accordance with embodiments described herein. Each of the dual selector valve assemblies 100, 200 described herein can receive a fluid sample to be analyzed and carrier fluid (e.g., mobile phase solvent), and can divert the fluids through a flow path selected from alternate flow paths (e.g., through different chromatographic columns) and back through the selector valve 100, 200 to a detection device.

According to embodiments described herein, the dual selector valve assembly 100, 200 includes a stator 110, 210 and a rotor 120, 220, which is rotated by the drive shaft of a motor assembly 130, 230. The stator 110, 210 and the rotor element 120, 220 of the selector valve assembly 100, 200 are both generally disk-shaped, and co-axially aligned together along the common longitudinal axis of the valve assembly. Common to all shear valve technology, the rotor 120, 220 is configured to rotate about the longitudinal axis while the stator 110, 210 is fixed. In the illustrated embodiments, an opposed side of the rotor 120, 220 is operably coupled to a drive shaft and motor assembly 130, 230 for selective rotational movement about the longitudinal axis. The rotor 120, 220 may be rotated about the longitudinal axis in either a clockwise or counter clockwise direction, relative to the stator 110, 210 to a selected position.

While the interfacing rotor face of the rotor 120, 220, and the opposed stator face of the stator element 110, 210, are preferably substantially planar, they need not be as long as the two surfaces sufficiently mesh and mate in a fluid-tight manner while permitting relative rotational movement about the longitudinal axis between discrete positions. As shown in FIGS. 2A and 2B, the stator 110, 210, the rotor 120, 220, and the motor assembly 130, 230 can be assembled together using screws.

Figure 3B:
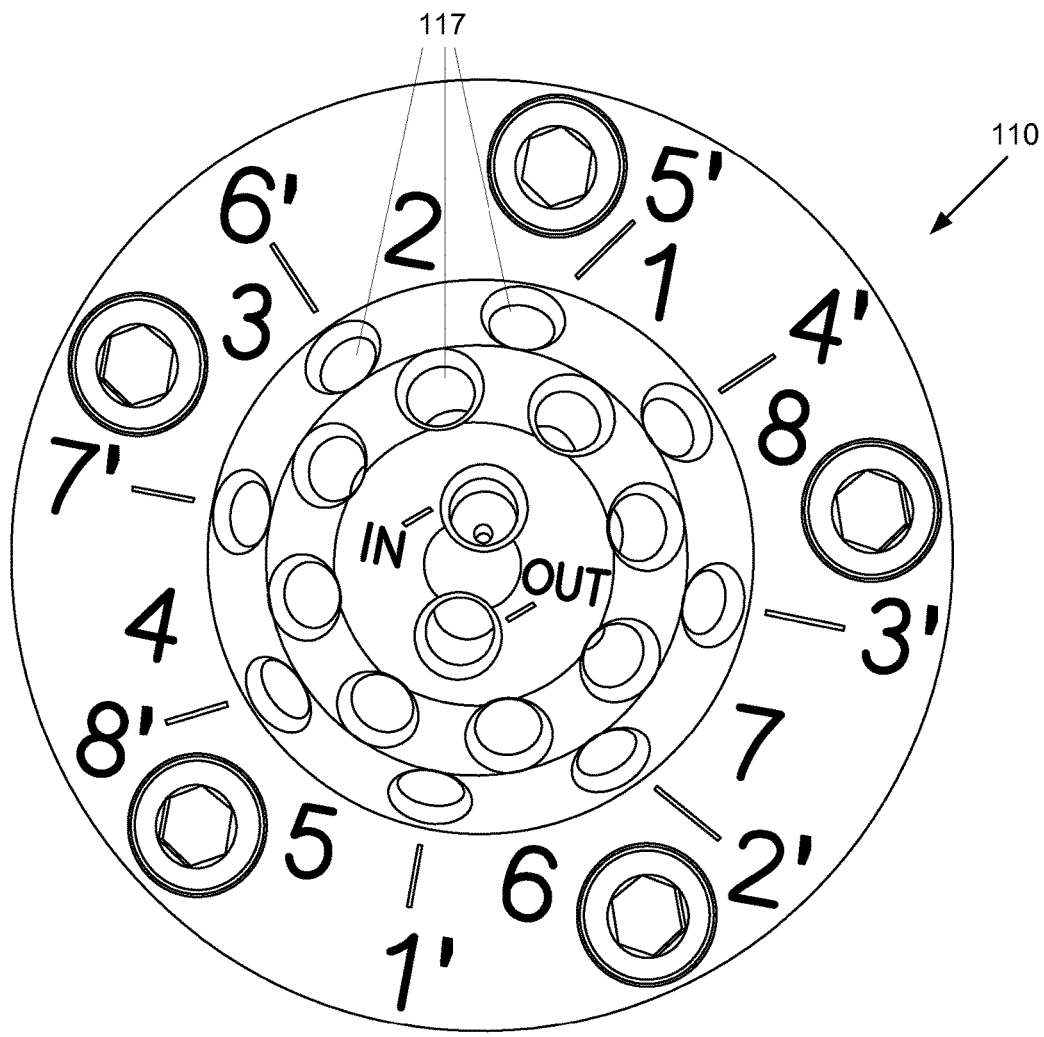
FIG. 3B is a front plan view of the front face of the stator shown in FIG. 3A.

An embodiment of a dual selector valve assembly 100 will be described with reference to FIGS. 3A-4. FIG. 3A is a simplified plan view of an embodiment of the stator face at the stator-rotor interface of the dual selector valve assembly 100, wherein the rotor face is transparently overlaid atop the stator face. As noted above, the rotor 110 is oriented to rotate about the longitudinal axis of the valve assembly. In this embodiment, the selector valve 100 allows selection of a flow path from among eight different columns 125 connected to corresponding ports (each column providing a flow path between ports 117 labeled 1 and 1', between ports 117 labeled 2 and 2', between ports 117 labeled 3 and 3', and so forth, on the stator front face). FIG. 3B is a plan view of the front face of the stator 110, showing the arrangement of the input and output ports 117 that correspond with the fluid passages 115 and their corresponding openings 112 on the dynamic or rear face of the stator 110.

FIG. 3C is a perspective view of the interfacing dynamic surfaces of the stator 110 and rotor 120. As shown in FIG. 3C, the interfacing surfaces of the stator 110 and rotor 120 are relatively small compared to the front face of the stator 110, where the chromatographic columns are fluidly connected to the stator 110. Each opening 112 on the dynamic surface of the stator 110 is connected by a passage 115 to a corresponding port 117 on the front face of the stator 110, as shown in FIG. 3D.

In FIG. 3A, the solid lines show features on the stator 110 and broken lines show features on the rotor 120. As used herein, the term "dynamic surface" is used to refer to the stator or rotor face that is at the stator-rotor interface. That is, the dynamic surface of the stator 110 is the rear, relatively flat face of the stator 110, and the dynamic surface of the rotor 120 is the front, relatively flat face of the rotor 120. It will be understood that only one subterranean passage 122a is fully shown and the other subterranean passage 122b is partially shown in FIG. 3D because FIG. 3D is a side cross-sectional view taken along the plane in which the first subterranean passage 122a is oriented.

As shown in FIGS. 3A and 3C, the dynamic surface of the stator 110 has two concentric rings of openings 112 to fluid passages 115. In the illustrated embodiment, an outer ring has eight openings 112 and an inner ring has eight openings 112. It will be understood that in other embodiments, the rings may have more or fewer openings 112 (and thus more or fewer chromatographic columns between the ports 117 on the front face of the stator 110). As noted above, each chromatographic column provides a flow path from port 1 on the front face of the stator to port 1' on the front face of the stator, port 2 to port 2', port 3 to port 3', and so forth. The broken lines in FIG. 3A represent the two subterranean passages 122a, 122b in the rotor 120.

The first subterranean passage 122a can be used to fluidly couple or bridge a common central opening 114 in the stator with a selected opening 112 on the inner ring of the stator 110. The central common opening 114 can be positioned on the rotational centerline on the dynamic surface of the stator 110 along the longitudinal axis. As is understood by those skilled in the art, positioning the central common opening 114 on the rotational centerline is better for dispersion.

By aligning a rotor opening on one end of the subterranean passage 122a with the common central stator opening 114 and aligning the rotor opening on the other end of the subterranean passage 122a with one of the stator openings 112 on the inner ring, fluid flow is permitted, via the first subterranean passage 122a of the rotor 120, between the central common opening 114 and a selected opening 112 on the inner ring of the stator 110. In contrast, the central common opening 114 can be fluidly decoupled from an opening 112 on the inner ring by rotating the rotor 120 such that the openings on the rotor 120 and the openings 112 on the stator 110 are not aligned. Thus, when the openings are not aligned, at least one end (i.e., the first rotor opening or the second rotor opening) of the subterranean passage 122a, terminates at a dead-end into the stator face preventing fluid flow therethrough. Similarly, at least one of the first common stator opening 114 or the second stator opening 112 on the inner ring terminates at a dead-end into the rotor face preventing fluid flow therebetween.

Similarly, the second subterranean passage 122b can be used to fluidly couple or bridge a collection ring 118 in the stator face with one of the stator openings 112 on the outer ring. It will be understood that the collection ring 118 is an annular groove that is formed into the dynamic surface of the stator 110. The collection ring 118 is coupled with the "out" port on the front face of the stator 110 by a passage 115 through the stator 110 with an opening 116 in the stator face at the collection ring 118. By aligning a rotor opening on one end of the subterranean passage 122b with the collection ring 118 and aligning the rotor opening on the other end of the subterranean passage 122b with one of the stator openings 112 on the outer ring, fluid flow is permitted, via the second subterranean passage 122b of the rotor 120, between a selected opening 112 on the outer ring of the stator 110 and the collection ring 118. In contrast, the collection ring 118 can be fluidly decoupled from a stator opening 112 on the outer ring by rotating the rotor 120 such that the openings on the rotor 120 and the openings 112 on the stator 110 are not aligned. Thus, when the openings are not aligned, at least one end (i.e., the first rotor opening or the second rotor opening) of the subterranean passage 122b, terminates at a dead-end into the stator face preventing fluid flow therethrough. Similarly, the stator opening 112 on the outer ring terminates at a dead-end into the rotor face preventing fluid flow between the stator opening 112 on the outer ring and the collection ring 118.

Accordingly, a fluid communication channel or bridge can be provided by the subterranean passages 122a, 122b of the rotor 120. Effectively, the fluid switching capabilities of the rotor 120 utilize all three dimensions, as opposed to just the two dimensions on the rotor face. Consequently, the same fluid switching capability of the rotor 120 can be provided, albeit occupying a significantly smaller surface area of rotor face. That is, rather than occupying valuable surface area of the rotor face (e.g., such as with a groove in rotor face), only four significantly smaller access openings on the rotor face are necessary in this embodiment.

The two subterranean passages 122a, 122b allow for a selector valve 100 that is capable of selecting from eight alternate flow paths using a single valve. The alternate flow paths are through a plurality of columns that fluidly connect openings 112 arranged around an inner ring to openings 112 arranged around an outer ring. As shown in FIG. 3A, the use of a collection ring 118 for the openings 112 on the outer ring allows the outer selector valve to "skip over" the openings 112 on the inner ring. As illustrated, in this embodiment, the entire face of the dynamic surface of the stator 110 can be used to fit in all of the openings necessary for eight different flow paths. Further, the subterranean passages provide a simple rotor/stator interface.

The two subterranean passages 122a, 122b can be the same size in some embodiments. That is, they can have the same length. However, in other embodiment, the two subterranean passages can have different lengths.

Figure 4:
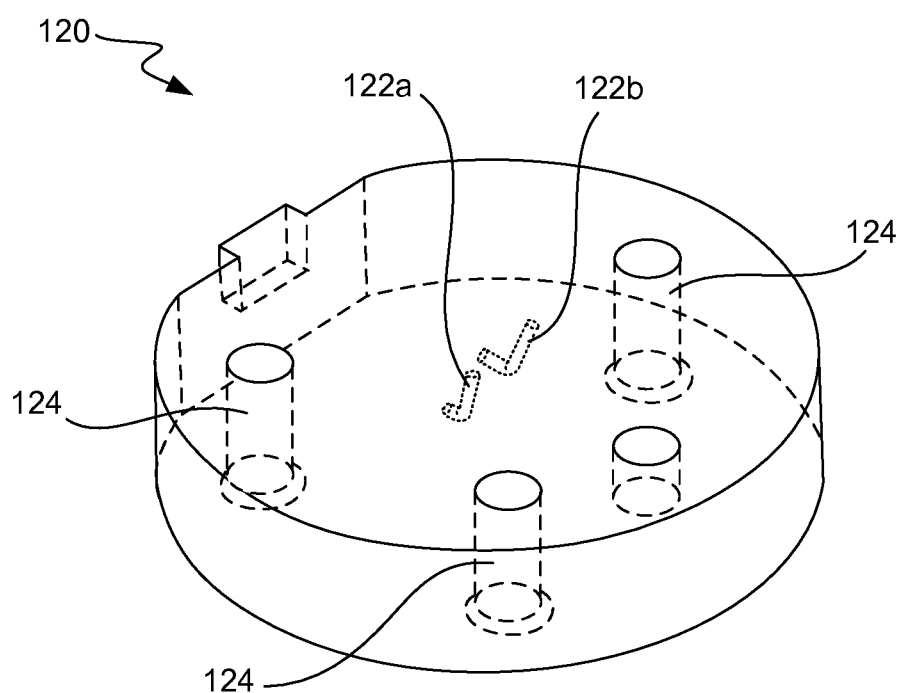
FIG. 4 is a perspective view of the rotor in accordance with the embodiment shown in FIGS. 3A-3D.

FIG. 4 is a detailed perspective view of the rotor 120. In the illustrated embodiment, the rotor 120 has two subterranean passages 122a, 122b. Each of the subterranean passages 122a, 122b is substantially V-shaped, as shown in FIG. 4, with each end having an opening on the dynamic surface of the rotor 120. When the openings on the dynamic surface of the rotor 120 are aligned with openings on the dynamic surface of the stator 110, fluid flow is permitted between the stator 110 and the rotor 120, and thus through the selected chromatographic column.

A column selector allows multiple users to select methods using the correct column for their assay and convenient washout and column storage. The dual selector valve 100 described herein can be used to select from eight different chromatographic columns in the illustrated embodiment. Thus, according to this embodiment, the valve 100 can receive fluid to be analyzed (with a carrier fluid) from a sample injector through the "in" port on the front face of the stator. The fluid then flows through a passage 115 in the stator 110 to the common central opening 114 and through the first subterranean passage 122a in the rotor 120. The fluid then flows out of the first subterranean passage 122a and through the selected opening 112 on the inner ring (e.g., 1, 2, 3, . . . ) of the stator 110 and through the stator and into the corresponding selected column (e.g., column 1, column 2, column 3, . . . ). The fluid then flows from the selected column and into the corresponding port on the front face of the stator 110, through the stator 110 and the corresponding opening 112 on the outer ring (e.g., 1', 2', 3', . . . ) of the dynamic surface stator 110, and through the second subterranean passage 122b. The fluid then exits the second subterranean passage 122b to the collection ring 118 to flow through the stator 110 and out the "out" port on the front face of the stator 110. From the "out" port, the fluid can then flow to the detector device.

For example, if column "1" is selected, then the fluid flows out of the first subterranean passage 122a to opening "1" on the inner ring and into column "1." The fluid then flows through column "1" and into port "1'" on the outer ring on the front face the stator to flow through the stator to the second subterranean passage 122b. Upon exiting the second subterranean passage 122b, the fluid flows to the collection ring 118 of the stator 110 and through the stator to the "out" port of the stator 110. It will be understood that in other embodiments, the fluid flow direction can be reversed by reversing the "in" and "out" ports on the front face of the stator 110

As shown in FIG. 4, in this embodiment, the rotor 120 has three through holes 124 that extend through the rotor from its front face to its rear face. These through holes 124 are provided for engagement with corresponding pins on the shaft and motor assembly 130 to enable rotation of the rotor 120. The subterranean passages 122a, 122b extend below the rotor's dynamic surface, as illustrated in FIGS. 3D and 4. In one embodiment, the subterranean passages 122a, 122b are each preferably contained substantially within a single plane, thereby simplifying the path as well as reducing the footprint of the subterranean passages within the rotor 120, as compared to a subterranean passage that snakes back and forth through the rotor body.

Each of the first subterranean passages 122a, 122b consists of two (a first and a second), substantially linear, passage components that both subtend and converge together, forming a generally V-shaped passage. This geometric shape is conducive to fabrication, and can be easily performed by drilling two substantially linear connecting passages, as shown. Each passage component subtends downwardly from the dynamic surface of the rotor 110, commencing at a rotor opening. For each subterranean passage, the opposed passage components converge toward one another until they intersect with one another at a bottom apex portion within the rotor body. Typically, the depth of the apex portion is no more than about ½ the height of the rotor body.

Each passage component is accordingly sized to accommodate sufficient fluid flow therethrough, and to facilitate opening alignment. The diameter of each passage may be slightly oversized relative to the diameter of the stator openings to be aligned therewith, for instance, in the range of about 2.2 mm to about 0.12 mm when the stator openings have a diameter in the range of about 2.0 mm to about 0.10 mm. The openings can be oval shaped. In fact, the oval shaped rotor openings will be naturally larger in one direction than the stator openings due to the angle of incidence of each passage component with the rotor face.

The angle of intersection between the two passage components of each subterranean passage at the apex portion, and its depth into the rotor body are generally dictated by the angle of incidence of each passage component relative to the plane $P_I$ of the rotor/stator interface. Generally, for the ease of fabrication, the angle of incidence of each passage component is substantially equal to one another, and typically in the range of about 60° to about 30°. Consequently, the angle of intersection between the passage components is about a right (90°) or an obtuse angle.

It follows, of course, that the greater (or steeper) the angle of incidence of either the first or second passage component, the smaller the angle of the intersection at the apex portion. Moreover, while the angle of incidence of the first and second passage components with the interface plane is preferably substantially equal to one another, thus dictating a substantially equal length of each passage component, but such equality is not necessary, as it may be modified depending upon the addition, and/or layout, of additional subterranean passages. In addition, these subterranean passages may be formed by fluid passages parallel to the axis of rotation (90 degrees to the plane P1) and all the way through the rotor 120. A connection slot on the backside of the rotor 120, which is sealed by the face of the shaft connects these two passages and completes the subterranean passage.

As mentioned, these two substantially linear passage components intersect one another at an apex portion. Such an angular, converging orientation of the passage components is conducive to simple fabrication via the application of conventional drilling techniques oriented at the proper angle of incidence. It will be appreciated, however, that other geometric configurations of the subterranean passages may be implemented. For example, a subterranean passage having a curvilinear profile may be provided, although it may be more difficult to fabricate in a solid rotor. One particular fabrication technique, for example, includes the application of a flexible tube member having the desired inner diameter dimensions. The rotor body then may be molded around the tubing, thus, encapsulating the tube and creating the subterranean passage with a curvilinear profile therein.

Figure 5A:
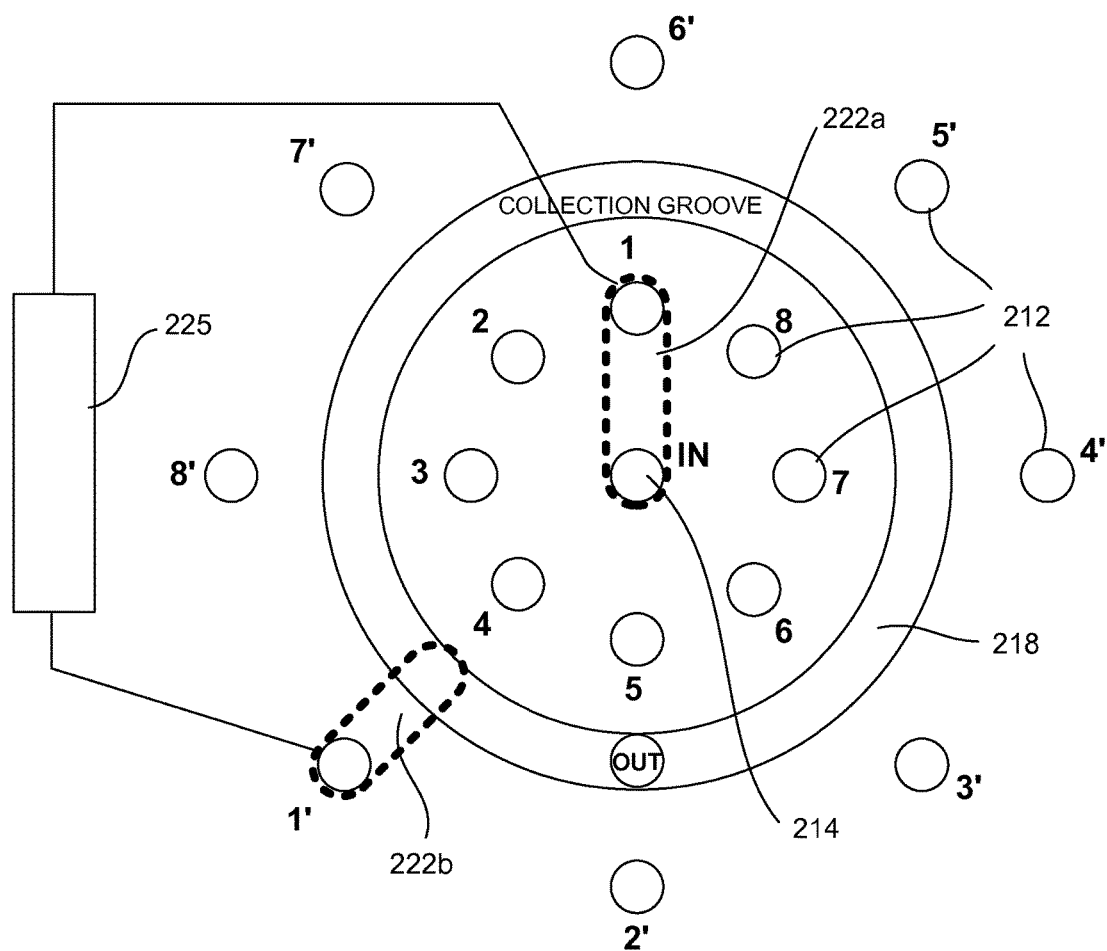
FIG. 5A is a simplified plan view of an embodiment of the stator face at the stator-rotor interface of another embodiment of a dual selector valve.
Figure 5B:
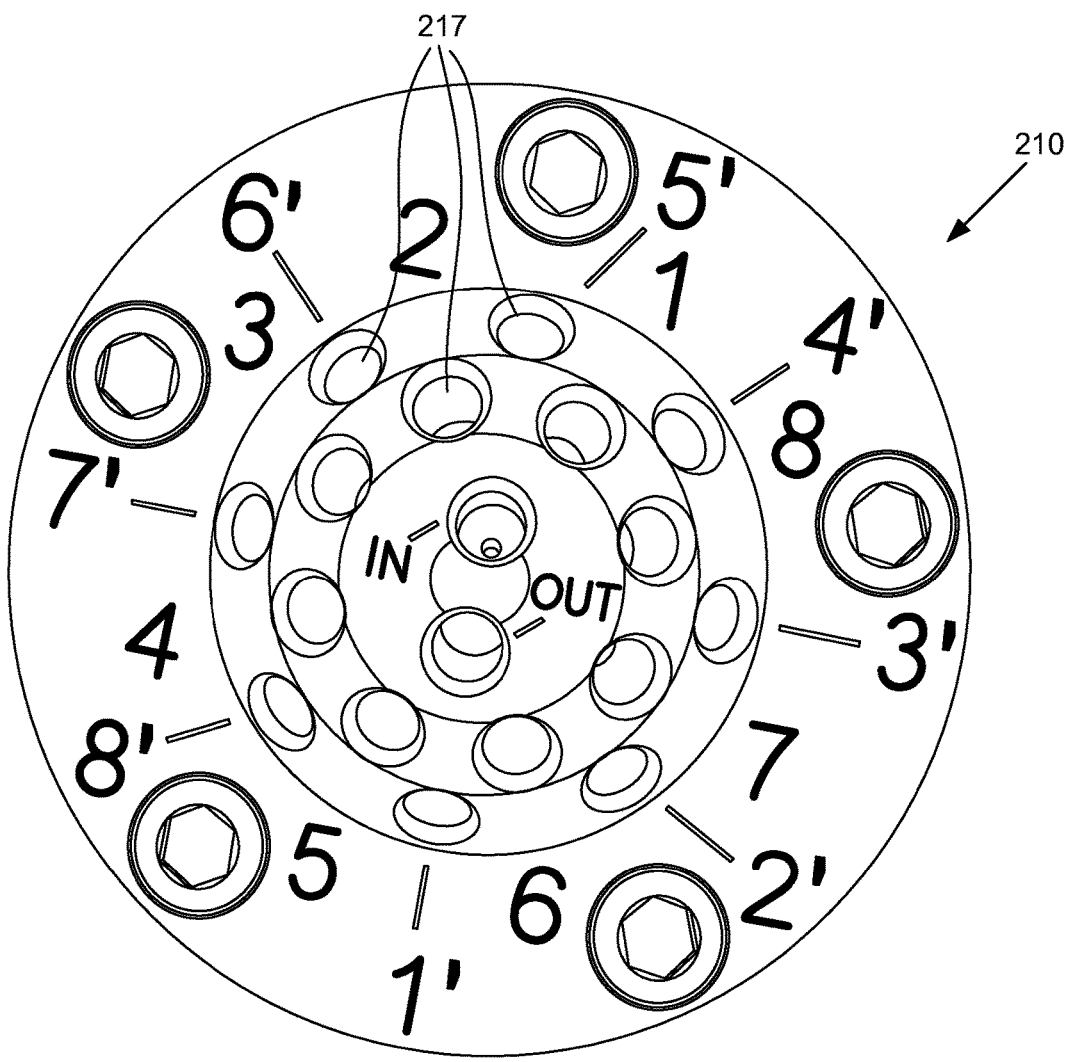
FIG. 5B is a front plan view of the front face of the stator shown in FIG. 5A.

Another embodiment of a dual selector valve assembly 200 will be described with reference to FIGS. 5A-6. FIG. 5A is a simplified plan view of an embodiment of the stator face at the stator-rotor interface of the dual selector valve assembly 200, wherein the rotor face is transparently overlaid atop the stator face. As noted above, the rotor 220 is oriented to rotate about the longitudinal axis of the valve assembly. In this embodiment, the selector valve 200 allows selection of a flow path from among eight different columns 225 connected to corresponding ports (each column providing a flow path between ports 212 labeled 1 and 1', between ports 212 labeled 2 and 2', between ports 212 labeled 3 and 3', and so forth, on the stator front face). FIG. 5B is a plan view of the front face of the stator 210, showing the arrangement of the input and output ports 217 that correspond with the fluid passages 215 and their corresponding openings 212 on the dynamic or rear face of the stator 210.

Figure 5C:
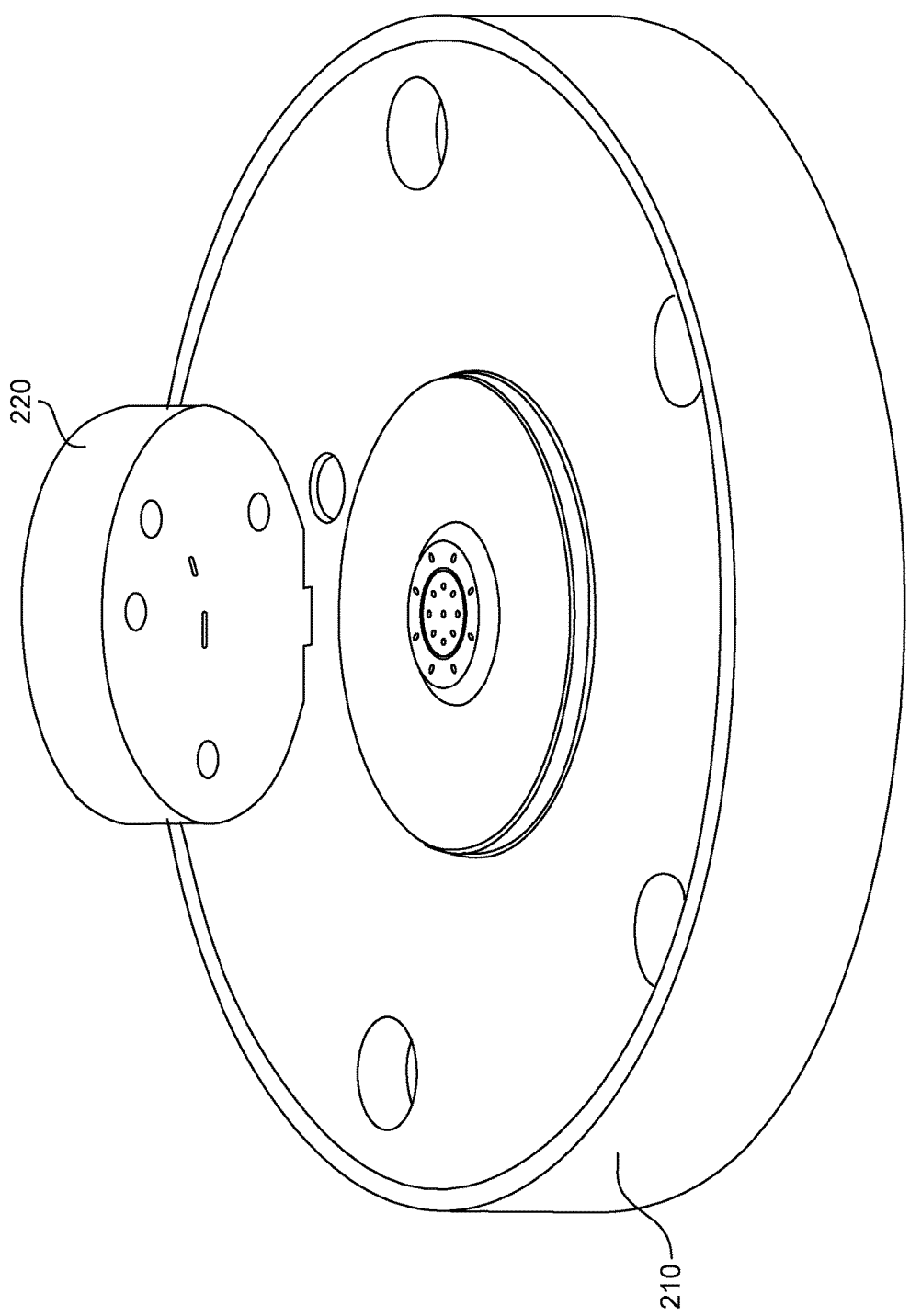
FIG. 5C is a perspective view of the interfacing dynamic surfaces of the stator and rotor shown in FIGS. 5A and 5B.
Figure 5D:
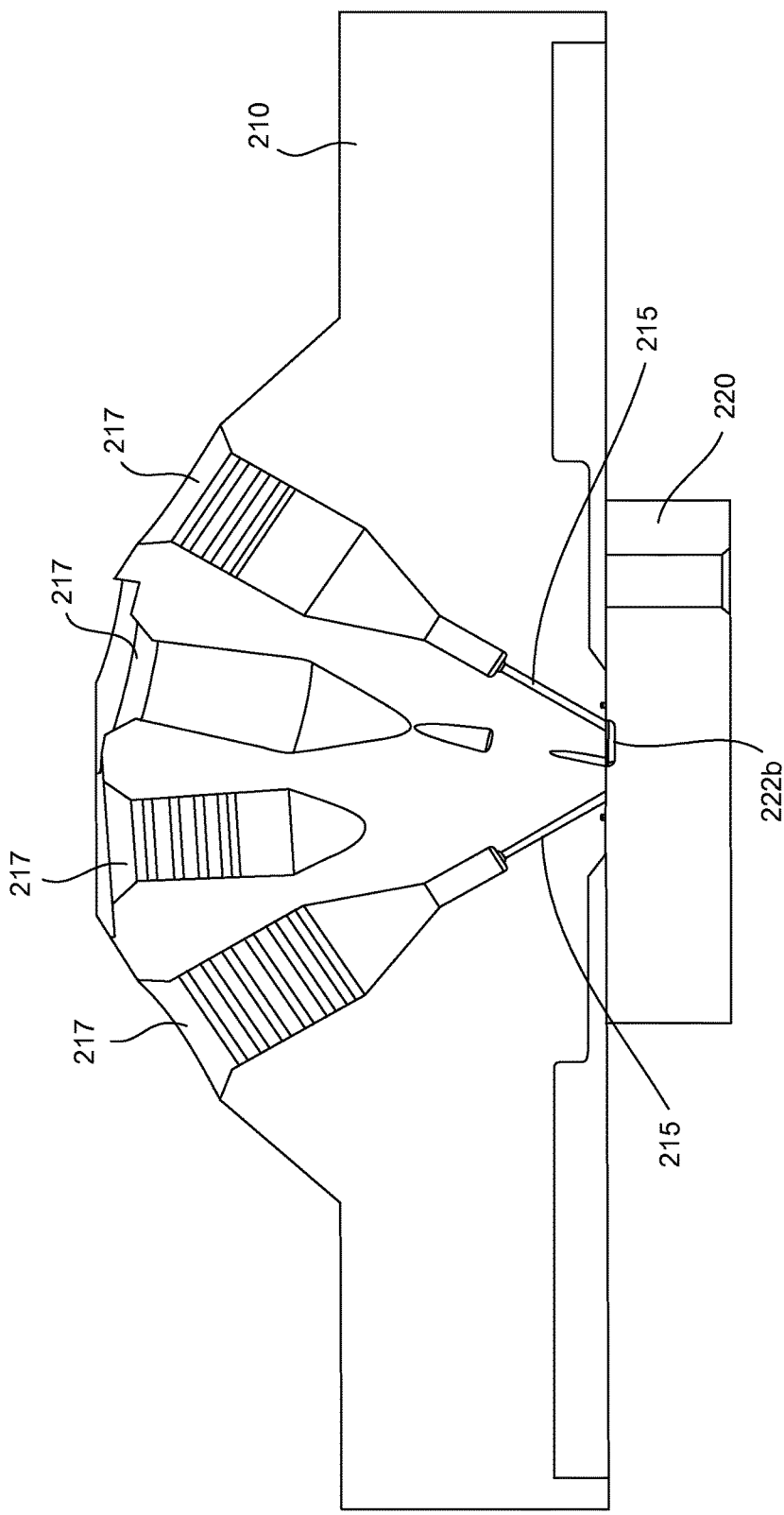
FIG. 5D is a side cross-sectional view of the dynamic surfaces of the stator and rotor of FIGS. 5A-5C, with the stator and rotor in fluid communication with one another.

FIG. 5C is a perspective view of the interfacing dynamic surfaces of the stator 210 and rotor 220. As shown in FIG. 5C, the interfacing surfaces of the stator 210 and rotor 220 are relatively small compared to the front face of the stator 210, where the chromatographic columns are fluidly connected to the stator 210. Each opening 212 on the dynamic surface of the stator 210 is connected by a passage 215 to a corresponding port 217 on the front face of the stator 210, as shown in FIG. 5D.

In FIG. 5A, the solid lines show features on the stator 210 and broken lines show features on the rotor 220. As used herein, the term "dynamic surface" is used to refer to the stator or rotor face that is at the stator-rotor interface. That is, the dynamic surface of the stator 210 is the rear, relatively flat face of the stator 210, and the dynamic surface of the rotor 220 is the front, relatively flat face of the rotor 220. The broken lines in FIG. 5A represent the grooves 122a, 122b that are formed in the dynamic surface of the rotor 220. It will be understood that only one groove 122b is fully shown and the other groove 122a is not shown in FIG. 5D because FIG. 5D is a side cross-sectional view taken along the plane in which one groove 122b is oriented.

As shown in FIGS. 5A and 5C, the dynamic surface of the stator 210 has openings 212 to fluid passages 215. The openings 212 are arranged in two concentric rings on the dynamic surface of the stator 210. In the illustrated embodiment, an outer ring has eight openings 212 and an inner ring also has eight openings 212. It will be understood that in other embodiments, the rings may have more or fewer openings 212 (and thus more or fewer chromatographic columns between the ports 217 on the front face of the stator 210). As noted above, each chromatographic column provides a flow path from port 1 on the front face of the stator to port 1' on the front face of the stator, port 2 to port 2', port 3 to port 3', and so forth. As noted above, the broken lines in FIG. 5A represent the two grooves 222a, 222b in the dynamic surface of the rotor 220.

The first grove 222a can be used to fluidly couple or bridge a common central opening 214 in the stator 210 with a selected opening 212 on the inner ring of the stator 210. The central common opening 214 can be positioned on the rotational centerline on the dynamic surface of the stator 210 along the longitudinal axis. As is understood by those skilled in the art, positioning the central common opening 214 on the rotational centerline is better for dispersion.

By aligning one end of the groove 222a with the common central stator opening 214 and aligning the other end of the groove 222a with one of the stator openings 112 on the inner ring, fluid flow is permitted, via the first groove 222a of the rotor 220, between the central common opening 214 and a selected opening 212 on the inner ring of the stator 210. In contrast, the central common opening 214 can be fluidly decoupled from an opening 212 on the inner ring by rotating the rotor 220 such that the ends of the groove 222a on the dynamic surface of the rotor 220 and the openings 212 on the stator 210 are not aligned. Thus, when the openings 212 of the stator 210 and the ends of the groove 222a are not aligned, at least one end (i.e., the first end of the groove 222a or the second end of the groove 222a) of the groove 222a, terminates at a dead-end into the stator face preventing fluid flow therethrough. Similarly, at least one of the first common stator opening 214 or the second stator opening 212 on the inner ring terminates at a dead-end into the rotor face preventing fluid flow therebetween.

Similarly, the second groove 222b can be used to fluidly couple or bridge a collection ring 218 in the stator face with one of the stator openings 212 on the outer ring. It will be understood that the collection ring 218 is an annular groove that is formed into the dynamic surface of the stator 210. As illustrated in FIG. 5A, the outer ring of openings 212, the collection ring 218, and the inner ring of openings 212 are concentric circles. As shown in FIG. 5A, the collection ring 218 is an annular groove positioned between the inner ring of openings 212 and the outer ring of openings 212 on the stator. Thus, the collection ring 218 is accordingly sized to accommodate sufficient fluid flow therethrough. In an embodiment, the width of the collection ring 218 is about 75% of the diameter of each stator opening 212. The depth of the collection ring 218 can be about 75% of the width of the collection ring 218.

The collection ring 218 is coupled with the "out" port on the front face of the stator 210 by a passage 215 through the stator 210 with an opening 216 in the stator face at the collection ring 218. By aligning one end of the groove 222b with the collection ring 218 and aligning the other end of the groove 222b with one of the stator openings 212 on the outer ring, fluid flow is permitted, via the second groove 222b of the rotor 220, between a selected opening 212 on the outer ring of the stator 210 and the collection ring 218. In contrast, the collection ring 218 can be fluidly decoupled from a stator opening 212 on the outer ring by rotating the rotor 220 such that the ends on the rotor 220 and the openings 212 on the stator 210 are not aligned. Thus, when the openings 212 on the stator 210 and the ends of the groove 222b are not aligned, at least one end (i.e., the first end of the groove 222b or the second end of the groove 222b) of the groove 222b, terminates at a dead-end into the stator face preventing fluid flow therethrough. Similarly, the stator opening 212 on the outer ring terminates at a dead-end into the rotor face preventing fluid flow between the stator opening 212 on the outer ring and the collection ring 218.

Accordingly, a fluid communication channel or bridge can be provided by the grooves 222a, 222b formed in the dynamic surface of the rotor 120. The two grooves 222a, 222b allow for a selector valve 200 that is capable of selecting from eight alternate flow paths using a single valve. The alternate flow paths are through a plurality of columns that fluidly connect openings 212 arranged around an inner ring to openings 212 arranged around an outer ring. As shown in FIG. 5A, the use of a collection ring 218 for the openings 212 on the outer ring allows the outer selector valve to "skip over" the openings 212 on the inner ring. As illustrated, in this embodiment, the entire face of the dynamic surface of the stator 210 can be used to fit in all of the openings necessary for eight different flow paths. Further, the grooves 222a, 222b provide a simple rotor/stator interface.

Figure 6:
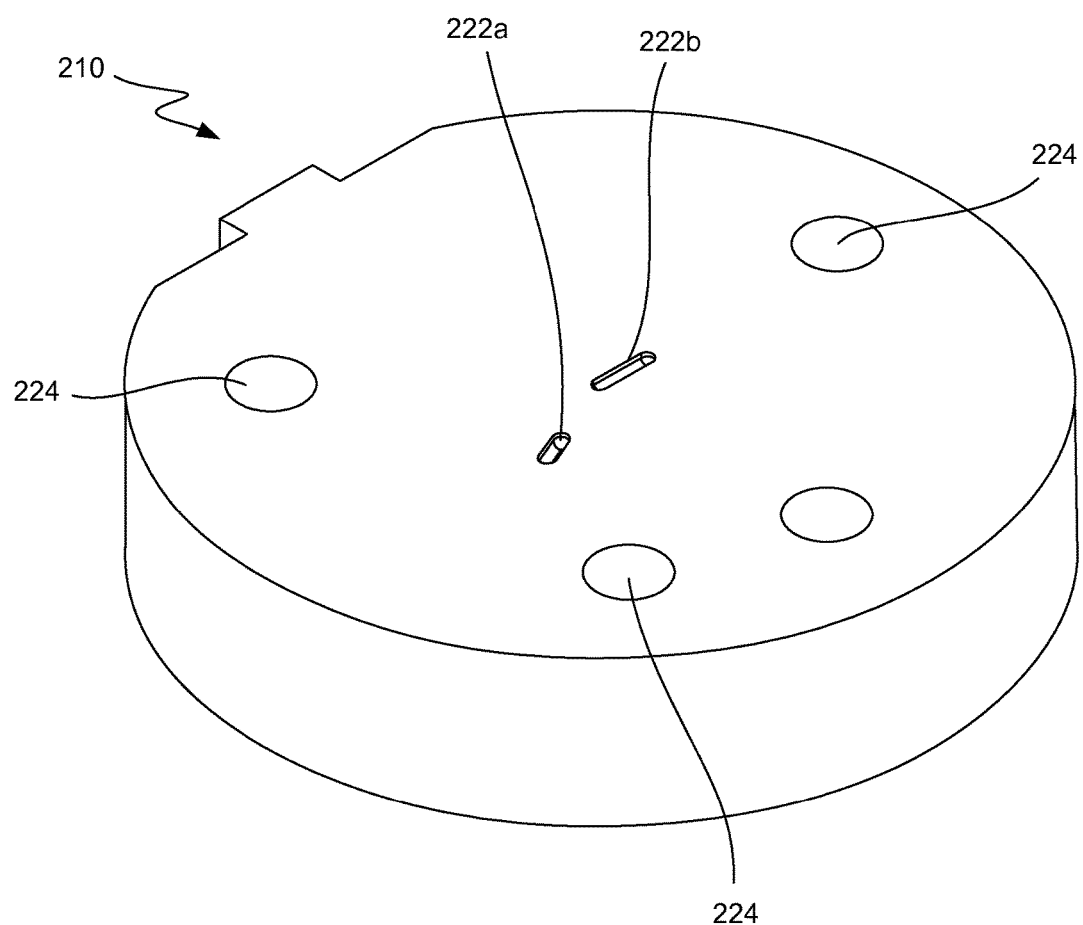
FIG. 6 is a perspective view of the rotor in accordance with the embodiment shown in FIGS. 5A-5D.

FIG. 6 is a detailed perspective view of the rotor 220. In the illustrated embodiment, the rotor 220 has two grooves 222a, 222b. Each of the grooves 222a, 222b is formed in the dynamic surface of the rotor 220, as shown in FIG. 4. When the ends of the grooves 222a, 222b on the dynamic surface of the rotor 220 are aligned with openings 212 on the dynamic surface of the stator 210, fluid flow is permitted between the stator 210 and the rotor 220, and thus through the selected chromatographic column A column selector allows multiple users to select methods using the correct column for their assay and convenient washout and column storage. The dual selector valve 200 described herein can be used to select from eight different chromatographic columns in the illustrated embodiment. Thus, according to this embodiment, the valve 200 can receive fluid to be analyzed (with a carrier fluid) from a sample injector through the "in" port on the front face of the stator. The fluid then flows through a passage 215 in the stator 210 to the common central opening 214 and through the first groove 222a in the rotor 220. The fluid then flows out of the first groove 222a and through the selected opening 212 on the inner ring (e.g., 1, 2, 3, . . . ) of the stator 210 and through the stator and into the corresponding selected column (e.g., column 1, column 2, column 3, . . . ). The fluid then flows from the selected column and into the corresponding port on the front face of the stator 210, through the stator 210 and the corresponding opening 212 on the outer ring (e.g., 1', 2', 3', . . . ) of the dynamic surface stator 210, and through the second groove 222b. The fluid then exits the second groove 222b to the collection ring 218 to flow through the stator 210 and out the "out" port on the front face of the stator 210. From the "out" port, the fluid can then flow to the detector device.

For example, if column "1" is selected, then the fluid flows out of the first groove 222a to opening "1" on the inner ring and into column "1." The fluid then flows through column "1" and into port "1" on the outer ring on the front face the stator to flow through the stator to the second groove 222b. Upon exiting the second groove 222b, the fluid flows to the collection ring 218 of the stator 210 and through the stator to the "out" port of the stator 210. It will be understood that in other embodiments, the fluid flow direction can be reversed by reversing the "in" and "out" ports on the front face of the stator 210

As shown in FIG. 6, in this embodiment, the rotor 220 has three through holes 224 that extend through the rotor from its front face to its rear face. These through holes 224 are provided for engagement with corresponding pins on the shaft and motor assembly 230 to enable rotation of the rotor 220. The grooves 222a, 222b are formed in the rotor's dynamic surface, as illustrated in FIGS. 5D and 6.

Each groove 222a, 222b is accordingly sized to accommodate sufficient fluid flow therethrough, and to facilitate opening alignment. The width of each groove 222a, 222b may be slightly oversized relative to the diameter of the stator openings to be aligned therewith, for instance, in the range of about 2.2 mm to about 0.12 mm when the stator openings have a diameter in the range of about 2.0 mm to about 0.10 mm. In an embodiment, the depth of each of the grooves 222a, 222b is about 75% of the width of each of the grooves 222a, 222b.

It will be appreciated that the forgoing embodiments are only a few illustrations of added functionality that can be applied using grooves or subterranean rotor passages. Other fluid channel configurations, therefore, can be easily implemented. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A dual selector valve assembly, comprising:
   a stator having a front face and a rear face, wherein the rear face comprises:
      a plurality of openings arranged along an inner ring;
      a plurality of openings arranged along an outer ring; and
      an annular collection groove formed in the rear face, wherein the annular collection groove forms a full circle; and
   a rotor having a front face configured to mate with the rear face of the stator, the rotor having a first fluid flow path and a second fluid flow path, the first fluid flow path comprising a first end and a second end, wherein the first end of the first fluid flow path is at a rotational center of the rotor and the second end of the first fluid flow path is configured to be aligned with a stator opening along the inner ring, and the second fluid flow path comprising a first end and a second end, wherein the first end of the second fluid flow path is configured to be aligned with the annular collection groove and the second end of the second fluid flow path is configured to be aligned with a stator opening along the outer ring.

2. The selector valve assembly of claim 1, wherein the first fluid flow path is a first groove and the second fluid flow path is a second groove.

3. The selector valve assembly of claim 1, wherein the first fluid flow path provides a flow path from an opening at a center of the rear face of the stator to a stator opening along the inner ring.

4. The selector valve assembly of claim 1, wherein the second fluid flow path provides a flow path from a stator opening along the outer ring to the annular collection groove.

5. The selector valve assembly of claim 1, further comprising:
   a passage from an input port on the front face of the stator to the opening at the center of the rear face of the stator; and
   a passage from the annular collection groove to an output port on the front face of the stator.

6. A dual selector valve assembly, comprising:
   a stator having a front face and a rear face, wherein the rear face comprises:
      a plurality of openings arranged along an inner ring;
      a plurality of openings arranged along an outer ring; and
      an annular collection groove formed in the rear face; and
   a rotor having a front face configured to mate with the rear face of the stator, the rotor having a first fluid flow path and a second fluid flow path, the first fluid flow path comprising a first end and a second end, wherein the first end of the first fluid flow path is at a rotational center of the rotor and the second end of the first fluid flow path is configured to be aligned with a stator opening along the inner ring, and the second fluid flow path comprising a first end and a second end, wherein the first end of the second fluid flow path is configured to be aligned with the annular collection groove and the second end of the second fluid flow path is configured to be aligned with a stator opening along the outer ring, wherein the first fluid flow path is a first subterranean passage that extends below a surface of the rotor and the second fluid flow path is a second subterranean passage that extends below the surface of the rotor.

7. The selector valve assembly of claim 6, wherein each of the subterranean passages comprises two substantially linear passage components that both subtend and converge together, forming a substantially V-shaped subterranean passage.

8. A dual selector valve assembly, comprising:
a stator having a front face and a rear face, wherein the rear face comprises:
  a plurality of openings arranged along an inner ring;
  a plurality of openings arranged along an outer ring; and
  an annular collection groove formed in the rear face; and
a rotor having a front face configured to mate with the rear face of the stator, the rotor having a first fluid flow path and a second fluid flow path, the first fluid flow path comprising a first end and a second end, wherein the first end of the first fluid flow path is at a rotational center of the rotor and the second end of the first fluid flow path is configured to be aligned with a stator opening along the inner ring, and the second fluid flow path comprising a first end and a second end, wherein the first end of the second fluid flow path is configured to be aligned with the annular collection groove and the second end of the second fluid flow path is configured to be aligned with a stator opening along the outer ring, wherein the annular collection groove, the inner ring, and the outer ring are concentric circles on the rear face of the stator.

9. The selector valve assembly of claim 8, wherein the annular collection groove is positioned between the inner ring and the outer ring.

10. The selector valve assembly of claim 8, wherein the inner ring is positioned between the annular collection groove and the outer ring.

11. A dual selector valve assembly, comprising:
a stator having a front face and a rear face, wherein the rear face comprises:
  a plurality of openings arranged along an inner ring;
  a plurality of openings arranged along an outer ring; and
  an annular collection groove formed in the rear face; and
a rotor having a front face configured to mate with the rear face of the stator, the rotor having a first fluid flow path and a second fluid flow path, the first fluid flow path comprising a first end and a second end, wherein the first end of the first fluid flow path is at a rotational center of the rotor and the second end of the first fluid flow path is configured to be aligned with a stator opening along the inner ring, and the second fluid flow path comprising a first end and a second end, wherein the first end of the second fluid flow path is configured to be aligned with the annular collection groove and the second end of the second fluid flow path is configured to be aligned with a stator opening along the outer ring, wherein the first fluid flow path is a first groove and the second fluid flow path is a second groove and wherein the first and second grooves are formed in the rear face of the rotor.

12. A selector valve assembly, comprising:
a stator having a front face and a rear face, wherein the rear face comprises:
  a plurality of openings arranged along an inner ring;
  a plurality of openings arranged along an outer ring; and
  an annular collection groove formed in the rear face, wherein the annular collection groove forms a full circle; and
a rotor having a front face configured to mate with the rear face of the stator, the rotor having a first subterranean passage and a second subterranean passage, the first subterranean passage comprising a first end and a second end, wherein the first end of the first subterranean passage is at a rotational center of the rotor and the second end of the first subterranean passage is configured to be aligned with a stator opening along the inner ring, and the second subterranean passage comprising a first end and a second end, wherein the first end of the second subterranean passage is configured to be aligned with the annular collection groove and the second end of the second subterranean passage is configured to be aligned with a stator opening along the outer ring.

13. The selector valve assembly of claim 12, wherein each of the subterranean passages comprises two substantially linear passage components that both subtend and converge together, forming a substantially V-shaped subterranean passage.

14. The selector valve assembly of claim 12, wherein the first subterranean passage provides a flow path from an opening at a center of the rear face of the stator to a stator opening along the inner ring and the second subterranean passage provides a flow path from a stator opening along the outer ring to the annular collection groove.

15. The selector valve assembly of claim 12, wherein the inner ring is positioned between the annular collection groove and the outer ring.

16. A selector valve assembly, comprising:
a stator having a front face and a rear face, wherein the front face comprises an outlet port for outputting all fluid from the selector valve assembly and wherein the rear face comprises:
  a plurality of openings arranged along an inner ring;
  a plurality of openings arranged along an outer ring; and
  an annular collection groove formed in the rear face; and
a rotor having a front face configured to mate with the rear face of the stator, the rotor having a first groove and a second groove, the first groove comprising a first end and a second end, wherein the first end of the first groove is at a rotational center of the rotor and the second end of the first groove is configured to be aligned with a stator opening along the inner ring, and the second groove comprising a first end and a second end, wherein the first end of the second groove is configured to be aligned with the annular collection groove and the second end of the second groove is configured to be aligned with a stator opening along the outer ring, wherein the annular collection groove is in fluid communication with the outlet port on the front face of the stator.

17. The selector valve assembly of claim 16, wherein the first groove provides a flow path from an opening at a center of the rear face of the stator to a stator opening along the inner ring and the second groove provides a flow path from a stator opening along the outer ring to the annular collection groove.

18. The selector valve assembly of claim 16, wherein the annular collection groove, the inner ring, and the outer ring are concentric circles on the rear face of the stator.

19. A selector valve assembly, comprising:
a stator having a front face and a rear face, wherein the rear face comprises:
  a plurality of openings arranged along an inner ring;
  a plurality of openings arranged along an outer ring; and
  an annular collection groove formed in the rear face, wherein the annular collection groove is positioned between the inner ring and the outer ring; and
a rotor having a front face configured to mate with the rear face of the stator, the rotor having a first groove and a second groove, the first groove comprising a first end and a second end, wherein the first end of the first groove is at a rotational center of the rotor and the second end of the first groove is configured to be aligned with a stator opening along the inner ring, and the second groove comprising a first end and a second end, wherein the first end of the second groove is configured to be aligned with the annular collection groove and the second end of the second groove is configured to be aligned with a stator opening along the outer ring.

20. A selector valve assembly, comprising:
a stator having a front face and a rear face, wherein the rear face comprises:
  a plurality of openings arranged along an inner ring;
  a plurality of openings arranged along an outer ring; and
  an annular collection groove formed in the rear face; and
a rotor having a front face configured to mate with the rear face of the stator, the rotor having a first groove and a second groove, the first groove comprising a first end and a second end, wherein the first end of the first groove is at a rotational center of the rotor and the second end of the first groove is configured to be aligned with a stator opening along the inner ring, and the second groove comprising a first end and a second end, wherein the first end of the second groove is configured to be aligned with the annular collection groove and the second end of the second groove is configured to be aligned with a stator opening along the outer ring, wherein each of the first and second grooves is formed in the rear face of the rotor.

* * * * *